United States Patent
Jamison et al.

(10) Patent No.: US 8,387,442 B2
(45) Date of Patent: Mar. 5, 2013

(54) METHODS TO CHARACTERIZE SAG IN FLUIDS

(75) Inventors: Dale E. Jamison, Humble, TX (US); Robert J. Murphy, Kingwood, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 522 days.

(21) Appl. No.: 12/685,348

(22) Filed: Jan. 11, 2010

(65) Prior Publication Data

US 2011/0167901 A1 Jul. 14, 2011

(51) Int. Cl.
*G01N 11/02* (2006.01)
(52) U.S. Cl. .............. 73/61.64; 73/61.63; 73/61.68
(58) Field of Classification Search ........... 73/53.01, 73/61.63, 61.64, 61.68
See application file for complete search history.

(56) References Cited

U.S. PATENT DOCUMENTS

| | | | |
|---|---|---|---|
| 3,016,734 A | 1/1962 | Kabelitz et al. | |
| 5,086,646 A | 2/1992 | Jamison et al. | |
| 6,330,826 B1 | 12/2001 | Meeten | |
| 6,584,833 B1 | 7/2003 | Jamison et al. | |
| 6,755,079 B1 | 6/2004 | Proett et al. | |
| 6,861,393 B2 * | 3/2005 | Temple et al. | 507/119 |
| 6,931,916 B2 | 8/2005 | Zamora et al. | |
| 7,081,437 B2 * | 7/2006 | Patel et al. | 507/103 |
| 7,845,212 B1 * | 12/2010 | Bi | 73/61.63 |
| 2003/0130596 A1 | 7/2003 | Von Der Goltz | |
| 2004/0261507 A1 | 12/2004 | Zamora et al. | |

FOREIGN PATENT DOCUMENTS

| GB | 2130728 | 6/1984 |
|---|---|---|
| GB | 2346702 | 8/2000 |

OTHER PUBLICATIONS

International Search Report in PCT/GB2011/000028, May 9, 2011.
T.H. Omland, A. Saasen, P.A. Amundsen, "Detection techniques determining weighting material sag in drilling fluid and relationship to rheology", Annual Trans. of the Nordic Rheology Society, vol. 15, 2007.
P.A. Bern, E. Van Oort, B. Neustadt, H. Ebeltoft, C. Zurdo, M. Zamora, K.S. Slater: "Barite sag: measurement, modeling, and management", SPE Drill & Completion, vol. 15, No. 1 Mar. 2000.
Saasen. A., Dawei Liu, Marken C. D., "Prediction of Barite Sag Potential of Drilling Fluids from Rheological Measurements," Drilling Conference, Amsterdam, (Feb. 28, 1995) pp. 663-671, 1995.

(Continued)

*Primary Examiner* — Daniel Larkin
(74) *Attorney, Agent, or Firm* — John W. Wustenberg; Baker Botts L.L.P.

(57) ABSTRACT

Systems and methods for direct and indirect measurement of the density of a fluid which exhibits sag characteristics is disclosed. The sag measurement system includes a test container for holding a fluid mixture to be analyzed and a suction port on the test container. A pump is coupled to the suction port for circulating the fluid mixture from the test container through a circulation loop. A measurement device is coupled to the circulation loop and a return port directs the fluid mixture from the circulation loop back to the test container at substantially the same vertical location as the suction port. The fluid mixture flowing through the circulation loop passes through the measurement device before returning to the test container through the return port. The measurement device is operable to monitor the particle distribution of the fluid mixture as it changes due to gravity.

5 Claims, 3 Drawing Sheets

OTHER PUBLICATIONS

William Dye, Terry Hemphill, William Gusler and Gregory Mullen, "Correlation of Ultra-Low Shear Rate Viscosity and Dynamic Barite Sag in Inver-Emulsion Drilling Fluids," SPE annual technical conference, Houston, TX, (Mar. 10, 1999), pp. 543-553, 1999.

Ahmadi Tehrani, Mario Zamora and David Power, "Role of Rheology in Barite Sag in SBM and OBM," American Association of Drilling Engineers, 2004 Drilling Fluids Conference, Houston, Texas, Apr. 6-7, 2004.

International Search Report in PCT/GB2009/002807, Feb. 12, 2009.

* cited by examiner

METHODS TO CHARACTERIZE SAG IN FLUIDS

BACKGROUND

Oilfield operations often entail the use of numerous fluid materials such as drilling fluids and fracturing fluids. A drilling fluid or "mud" is a specially designed fluid that is circulated in a wellbore or borehole as the wellbore is being drilled in a subterranean formation to facilitate the drilling operation. The various functions of a drilling fluid include removing drill cuttings from the wellbore, cooling and lubricating the drill bit, aiding in support of the drill pipe and drill bit, and providing a hydrostatic head to maintain the integrity of the wellbore walls and prevent well blowouts. Specific drilling fluid systems are selected to optimize a drilling operation in accordance with the characteristics of a particular geological formation.

A drilling fluid typically comprises water and/or oil or synthetic oil or other synthetic material or synthetic fluid as a base fluid, with solids in suspension. A non-aqueous based drilling fluid typically contains oil or synthetic fluid as a continuous phase and may also contain water dispersed in the continuous phase by emulsification so that there is no distinct layer of water in the fluid. Such dispersed water in oil is generally referred to as an invert emulsion or water-in-oil emulsion.

A number of additives may be included in such drilling fluids and invert emulsions to enhance certain properties of the fluid. Such additives may include, for example, emulsifiers, weighting agents, fluid-loss additives or fluid-loss control agents, viscosifiers or viscosity control agents, and alkali.

The density of the drilling mud is closely maintained in order to control the hydrostatic pressure that the mud exerts at the bottom of the well. If the mud is too light, formation fluids, which are at higher pressures than the hydrostatic pressure developed by the drilling mud, can enter the wellbore and flow uncontrolled to the surface, possibly causing a blowout. If the mud is too heavy, then the hydrostatic pressure exerted at the bottom of the wellbore can reduce the rate at which the drill bit will drill the hole. Additionally, excessive fluid weights can fracture the formation causing serious wellbore failures. In some cases, failure can cause drilling fluid to be lost to the formation, depleting the drilling fluid, leading to under pressurization or well control problem. Thus, the control of the solids content of the drilling fluid is very crucial to the overall efficiency and safe operation of the rig.

In the most common applications, the density of the drilling mud is increased by adding particulate weighting agents, such as barite and hematite. These particles are prone to settling within the drilling mud under the influence of gravity. This settling is known in the industry as "sag" or "barite sag" and is a persistent and potentially serious drilling problem that occurs most prevalently in directional wells drilled with weighted drilling muds.

Sag can occur, for example, when circulation of the fluid is stopped for a period of time, e.g., when the drill string must be tripped from the well, and is caused by the resulting settling or stratification of the fluid whereby "heavy spots" and "light spots" develop. Sag can also involve movement or shifting of these heavy and light fractions, particularly the "heavy spots", where components such as barite have become concentrated. Sag may not occur throughout an entire well, but its occurrence in even a small section of the well can cause the problems referred to below. Generally, higher temperatures exacerbate sag while higher pressures tend to retard sag.

Sag is not particularly problematic if the well is vertical or near vertical. The magnitude of the problem may be smaller if the well, or the section of the well in question, is nearly horizontal. However, if the well or a section thereof has a relatively high deviation angle (i.e., angle with respect to vertical), but falling well short of 90 degrees, sag problems can become particularly severe. The advent and recent strides in extended reach drilling, which have resulted in relatively highly deviated wells, e.g., wells with deviation angles of 20 degrees or more, has brought sag problems into focus in the drilling industry.

Sag of the weighting agents in a fluid used in oil field operations can cause large density variations that often lead to significant wellbore pressure management problems and potentially, wellbore failure. Additionally, fluid sag can lead to sticking of drill pipe, difficulty in re-initiating and/or maintaining proper circulation of the fluid, possible loss of circulation and disproportionate removal from the well of lighter components of the fluid.

A number of solutions have been proposed for analyzing the sag properties of a fluid. For instance, U.S. Pat. No. 6,584,833 to Jamison et al. (hereinafter "'833 patent") discloses a method of determining the settling rate of a fluid and is incorporated by reference herein in its entirety. However, it is desirable to have a reliable method for measuring and/or monitoring the sag of the weighting agents in the field.

FIGURES

Some specific example embodiments of the disclosure may be understood by referring, in part, to the following description and the accompanying drawings.

Figure 1:
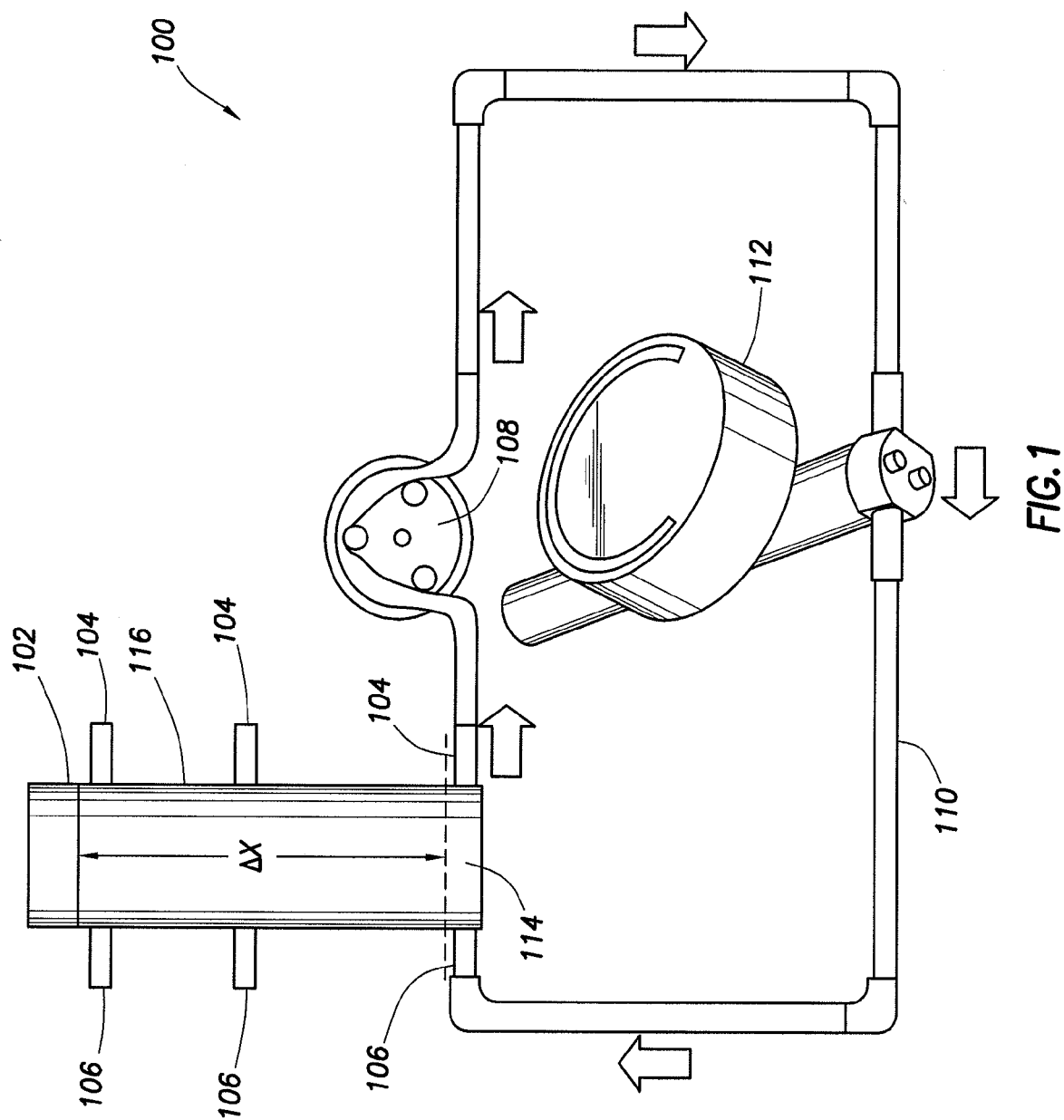
FIG. 1 is a Sag Measurement System in accordance with an exemplary embodiment of the present invention.

While embodiments of this disclosure have been depicted and described and are defined by reference to example embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

SUMMARY

The present invention is directed to systems and methods for monitoring fluids used in subterranean operations. More particularly, the present invention is directed to systems and methods for direct and indirect measurement of the density of a fluid which exhibits sag characteristics.

In one embodiment, the present invention is directed to a sag measurement system comprising: a test container for holding a fluid mixture to be analyzed; a suction port on the test container; a pump coupled to the suction port for circulating the fluid mixture from the test container through a circulation loop; a measurement device coupled to the circulation loop; and a return port for directing the fluid mixture from the circulation loop back to the test container at substantially same vertical location as the suction port; wherein gravity changes a particle distribution of the fluid mixture with time; wherein the measurement device is operable to monitor the particle distribution of the fluid mixture; and wherein the fluid mixture flowing through the circulation loop passes through the measurement device before returning to the test container through the return port.

In another exemplary embodiment, the present invention is directed to a method of analyzing sag performance comprising: placing a first fluid mixture to be analyzed in a test container; and circulating the first fluid mixture through a first circulation loop including a density transducer; wherein the first fluid mixture enters and exits the first circulation loop through a first set of ports of the test container; and monitoring a change in density of the first fluid mixture as a function of time.

In another exemplary embodiment, the present invention is directed to a method of characterizing sag performance of a fluid mixture comprising: determining a first density of the fluid mixture at a first point in time; inferring a first volume fraction of a solid component of the fluid mixture at the first point in time; determining a second density of the fluid mixture at a second point in time; inferring a second volume fraction of the solid component of the fluid mixture at the second point in time; and using the first volume fraction and the second volume fraction to determine the settling velocity of the solid component in the fluid mixture.

In another exemplary embodiment, the present invention is directed to a method of characterizing sag performance by determining a maximum particle size of a solid component that may be suspended in a fluid portion of a fluid mixture, comprising: placing a fluid mixture in a test container having a lower portion and a higher portion; wherein an suction port and a return port are placed at the lower portion of the test container for directing the fluid mixture to a circulation loop including a density transducer; wherein the fluid comprises a test section corresponding to the higher portion of the test container and a mixed section corresponding to the lower portion of the test container; determining a first density of the fluid mixture in the mixed section at a first point in time using the density transducer; inferring a first volume fraction of the solid component of the fluid mixture in the mixed section at the first point in time; determining a second density of the fluid mixture in the mixed section at a second point in time using the density transducer; inferring a second volume fraction of the solid component of the fluid mixture in the mixed section at the second point in time; determining a difference between the second volume fraction and the first volume fraction; determining an increase in mass of the solid component of the fluid mixture in the mixed section using the difference between the second volume fraction and the first volume fraction; and using a particle size distribution of the solid component and the increase in mass of the solid component in the fluid mixture in the mixed section to determine the particle size range of the solid component that may be suspended in the fluid portion.

The features and advantages of the present disclosure will be readily apparent to those skilled in the art upon a reading of the description of exemplary embodiments, which follows.

DESCRIPTION

The present invention is directed to systems and methods for monitoring fluids used in subterranean operations. More particularly, the present invention is directed to systems and methods for direct and indirect measurement of the density of a fluid which exhibits sag characteristics.

The details of the present invention will now be discussed with reference to the figures. FIG. 1 depicts a Sag Measurement System ("SMS") in accordance with an exemplary embodiment of the present invention, designated generally with reference numeral 100. The SMS includes a test container 102 which holds the fluid to be analyzed. As would be apparent to those of ordinary skill in the art, with the benefit of this disclosure, the container 102 may have any suitable shape and be positioned at angles other than vertical. In one exemplary embodiment, the fluid may be a drilling fluid. In one embodiment, the test container 102 may be heated and/or pressurized to simulate different operating conditions. Moreover, in one embodiment, the container 102 may have a means to shear or agitate the fluid being analyzed such that vertical mixing is minimized. For instance, in one embodiment, the container 102 may contain a rotating concentric rod which would be operable to shear the fluid being analyzed at a known and controlled rate.

The test container 102 may have one or more sets of two ports 104, 106. One of the ports in each set is a suction port 104 and the other is a return port 106. In some embodiments the function of the ports could be reversed periodically. The suction port 104 may be connected to a pump 108 which circulates or reciprocates the drilling fluid being analyzed through the system. As would be appreciated by those of ordinary skill in the art, a number of different pumps may be used in the system. For instance, the pump may be a peristaltic pump, a gear pump, a centrifugal pump, a diaphragm pump or a piston pump. In all cases the circulation is controlled and the ports 104 and 106 are positioned such that the vertical mixing of fluid in container 102 is minimized. In the preferred embodiment, the ports 104 and 106 are tangentially aligned with inside diameter of 102. The pump 108 directs the drilling fluid through the circulation loop 110. Specifically, the pump 108 directs the drilling fluid to a density transducer 112 and then back to the test container 102 through the return port 106. Although FIG. 1 depicts a density transducer placed in the circulation loop 110, in another embodiment, other measurement devices may be used. For instance, the measurement device used may be one or a combination of a density transducer, a rheometer or a viscometer. In some embodiments, multiple instrumented loops may be used.

When using the SMS 100, the drilling fluid in the lower portion 114 of the test container 102 is continuously circulated through the system. This keeps the drilling fluid mixed so that no or minimal solids settle out of the fluid at the bottom of the test container 102 or the loop 110. Additionally, the fluid in the upper part (unmixed) 116 of the test container 102 is not affected by the flow and mixing in the lower section 114. As the sag or settling process proceeds, the density in the lower section of the test container 102 increases. The rate at which the density in the lower section of the test container 102 increases is a function of the sag resistance properties of the drilling fluid being tested. Measurement loops above the bottom may have increasing or decreasing density, depending on vertical location as well as the sag tendency of the test fluid at test conditions.

When using the SMS 100, a drilling fluid to be tested is placed in the test container 102. The pump 108 then circulates the drilling fluid through the loop 110 and the density of the sample may be measured by the density transducer 112. As the solid component of the drilling fluid settles, the density of the drilling fluid being circulated through the SMS 100 increases. The change in the density of the drilling fluid may be monitored as a function of time. In one embodiment, monitoring may be performed by an automatic system such as, for example, a computer device.

In one embodiment, the data obtained from the SMS 100 may be used to compare the sag performance of different drilling fluids. Specifically, a user may compare the change in density of different drilling fluids using the SMS 100 to determine which has a better sag performance. In this embodiment, once the density of a first fluid is monitored over time in the SMS 100, the first fluid is removed from the test container 102. The system may then be cleaned by passing a cleaning fluid through it. As would be appreciated by those of ordinary skill in the art, with the benefit of this disclosure, if the first fluid is oil based, an appropriate solvent may be used as the cleaning fluid. In contrast, if the first fluid is water based, then water may be used as the cleaning fluid. A second fluid may then be placed in the test container 102 and circulated through the density transducer 112 of the SMS 100. The change in density of the second fluid over time may then be monitored and the density change of the two fluids may be compared to determine which has a better sag performance. As would be appreciated by those of ordinary skill in the art, with the benefit of this disclosure, the fluid which has a lower change in density over time has a better sag performance. Accordingly, a user may compare the magnitude of the differential density of one drilling fluid to that of another drilling fluid as a way to compare sag performance.

In one exemplary embodiment, the multiple sets of ports 104, 106 may be used to obtain similar measurements at different vertical locations within the container 102, allowing an analysis and monitoring of the changes in the density of the drilling fluid at different locations in the container 102. Depending on the user preferences, the measurements at the different sets of ports 104, 106 may be obtained sequentially or simultaneously. Although only three sets of ports 104, 106 are depicted in FIG. 1, as would be apparent to those of ordinary skill in the art, with the benefit of this disclosure, any numbers of sets of ports 104, 106 may be used.

As would be appreciated by those of ordinary skill in the art, with the benefit of this disclosure, there is a limit on the increase in the density of the drilling fluid at the bottom area of the test container 102. This limit is due to the availability of solids that can settle in the finite volume of the test container 102 as well as the maximum packing density of the settled materials. Moreover, not all the solid particles are the same size. As a result, all the solid particles do not settle at the same rate and some may not settle at all.

As would be appreciated by those of ordinary skill in the art, with the benefit of this disclosure, if the drilling fluids being compared have different densities, the comparison becomes more difficult due to the availability of the solids to settle. For instance, when comparing a first drilling fluid with a low density to a second drilling fluid with a higher density, the settling rate of the solid components can actually be higher in the lower density drilling fluid. However, the total density change of the samples over time may not accurately indicate the higher settling rate of the barite in the first drilling fluid.

Accordingly, in another exemplary embodiment, fluids of various densities may be compared by calculating the average settling velocity of the solid component(s) of the drilling fluids. In one exemplary embodiment, the solid component may be barite solids. The calculation of the settling velocity provides a method to compare results from fluids having different densities as well as providing a basis for comparison to the Dynamic High Angle Settling Test which is disclosed in the '833 patent.

In this exemplary embodiment, the density of the drilling fluid is used to infer a barite volume fraction. The change in the volume fraction of the barite is then used to calculate a settling velocity for the sample. The sum of volumes of the drilling fluid components is then used to calculate a barite volume fraction. Specifically, the bulk fluid density is obtained using the following equation:

$$\rho = \phi D_{barite} + (1-\phi)(1-(\% \text{ Oil}/100))D_{brine} + (1-\phi)(\% \text{ Oil}/100)D_{oil} \quad \text{[Eq. 1]}$$

where $\rho$ is the bulk fluid density; $\phi$ is the volume fraction of settling barite and/or solids; % Oil is the percent volume of oil in the liquid phase. As would be appreciated by those of ordinary skill in the art, with the benefit of this disclosure, for an all-water fluid with no oil, % Oil is 0; for an all-oil fluids with no water or brine the % Oil is 100; $D_{barite}$ is the average density of the settling barite and/or other solids; $D_{brine}$ is the density of the brine or water phase; and $D_{oil}$ is the density of the oil phase. The above equation may be rearranged as:

$$\phi = (\rho - K)/(D_{barite} - K) \quad \text{[Eq. 2]}$$

where $K = [(1-\% \text{ Oil}/100)D_{brine}] + [(\% \text{ Oil}/100)D_{oil}]$

Accordingly, in one exemplary embodiment, the drilling fluid sample to be analyzed may be put through the SMS 100 to determine the density change for a finite time. The data obtained may then be used to calculate a settling velocity by making the following assumptions for the case where the suction and the return ports are located at the bottom: (1) that the velocity of all the solids settling in the unmixed portion of the test container is a constant velocity; (2) that the change in the barite volume fraction for the mixed portion is comprised of the barite initially evenly distributed in the unmixed section of the test container; (3) that all solids have the same specific gravity; and (4) that the settled fluid has not reached the maximum packing density.

Accordingly, the settling rate may be obtained using the following equation:

$$[(\phi_t - \phi_i)\text{Vol}_{mixed}]/t = \phi_i \times \pi R^2 \Delta X/t \quad \text{[Eq. 3]}$$

which can be rearranged as:

$$\Delta X/t = V_{barite} = [(\phi_t - \phi_i)\text{Vol}_{mixed}]/[\phi_i \pi R^2 t] \quad \text{[Eq. 4]}$$

where $\phi_t$ is the volume fraction of the barite and/or settleable solids in the mixed portion at some elapsed time, t; $\phi_i$ is the initial volume fraction of the barite and/or settleable solids; $\text{Vol}_{mixed}$ is the volume of the mixed portion of the test system, including the volume of the lower portion 114 of the test container 102, the pump 108, the tubing loop 110 and the density transducer 112; R is the radius of the test container; $\Delta X$ is the height of the unmixed portion of the test fluid in the container above the mixed zone that the average solid particle settles through to reach the mixed volume; and $V_{barite}$ is the average settling rate of the barite and/or solids in the sample.

As would be appreciated by those of ordinary skill in the art, with the benefit of this disclosure the velocities obtained by this method represent the average settling rate of the solids in the drilling fluid sample analyzed. Additionally, as discussed above and depicted in FIG. 2, the density of the fluid sample being analyzed reaches a certain maximum limit over time. As a result, the settling velocity calculated in accordance with methods disclosed herein will also diminish with time implying that only a portion of the barite in the drilling fluid in the upper test section will settle.

In one exemplary embodiment, the PSD (Particle Size Distribution) curve of the barite (and/or other solid components used in a fluid to be analyzed) may be used in conjunction with the system and methods disclosed herein to determine the maximum particle size which a test fluid can reliably suspend. As would be appreciated by those of ordinary skill in the art, the particles having different sizes will not settle at the same rate. Therefore, assuming that all the density change in the lower portion 114 of the test container 102 is due to the larger and more mobile particles, then the apparent particle size that does not settle in the test fluid may be calculated. Once it is determined what particle size does not settle in the test fluid, that information may be used as a design method to determine the best grind size range for commercial barite for sag performance.

The calculations used in determining the relationship between particle size and settling may be carried out under the assumption that there was little or no particle attrition relative to initial PSD data of the fluid weighting agents and the settling particles were all of the same specific gravity. However, if barite or other PSD data had been obtained for the fluid prior to testing, one could determine the particle size at which the fluid structure and particle to particle interactions would provide sufficient settling inhibition for practical use.

As would be appreciated by those of ordinary skill in the art, the comparison of the apparent non-settling particle diameter of one fluid may be compared to that of another. That comparison may be used as a test measure to determine which particle size limit is best suited for a given application. Specifically, the larger the particle size that may be suspended by a fluid, the more sag resistant the fluid is. Moreover, as would be appreciated by those of ordinary skill in the art, the system and methods disclosed herein may be used to determine the relative volume fraction of the solid component that is mobile to that which is not mobile. The results obtained using the system and methods disclosed herein may be used to determine the basic parameters required to develop a software model to determine the practical engineering models for the sagging of solid particles.

In another exemplary embodiment of the present invention, in addition to obtaining density measurement, the SMS 100 may also be used to measure rheology of a fluid being tested. As would be appreciated by those of ordinary skill in the art, with the benefit of this disclosure, in this embodiment, the viscosity of a fluid increases as the solids' volume fraction increases due to barite sag.

Although the present invention is disclosed in the context of drilling fluids, as would be appreciated by those of ordinary skill in the art, with the benefit of this disclosure, the system and methods disclosed herein may be used in conjunction with any fluids where it would be desirable to characterize and/or monitor fluid sag. For instance, the present invention may be used in conjunction with any particulate laden fluid that exhibits particle sag or settling tendencies such as cementing fluids, spacer fluids, fracturing fluids and gravel pack fluids. Moreover, although the present invention is disclosed as using barite as the solid component, as would be appreciated by those of ordinary skill in the art, with the benefit of this disclosure, the solid component of the fluid being analyzed may be any solid suitable for the intended application.

Example I

Figure 2:
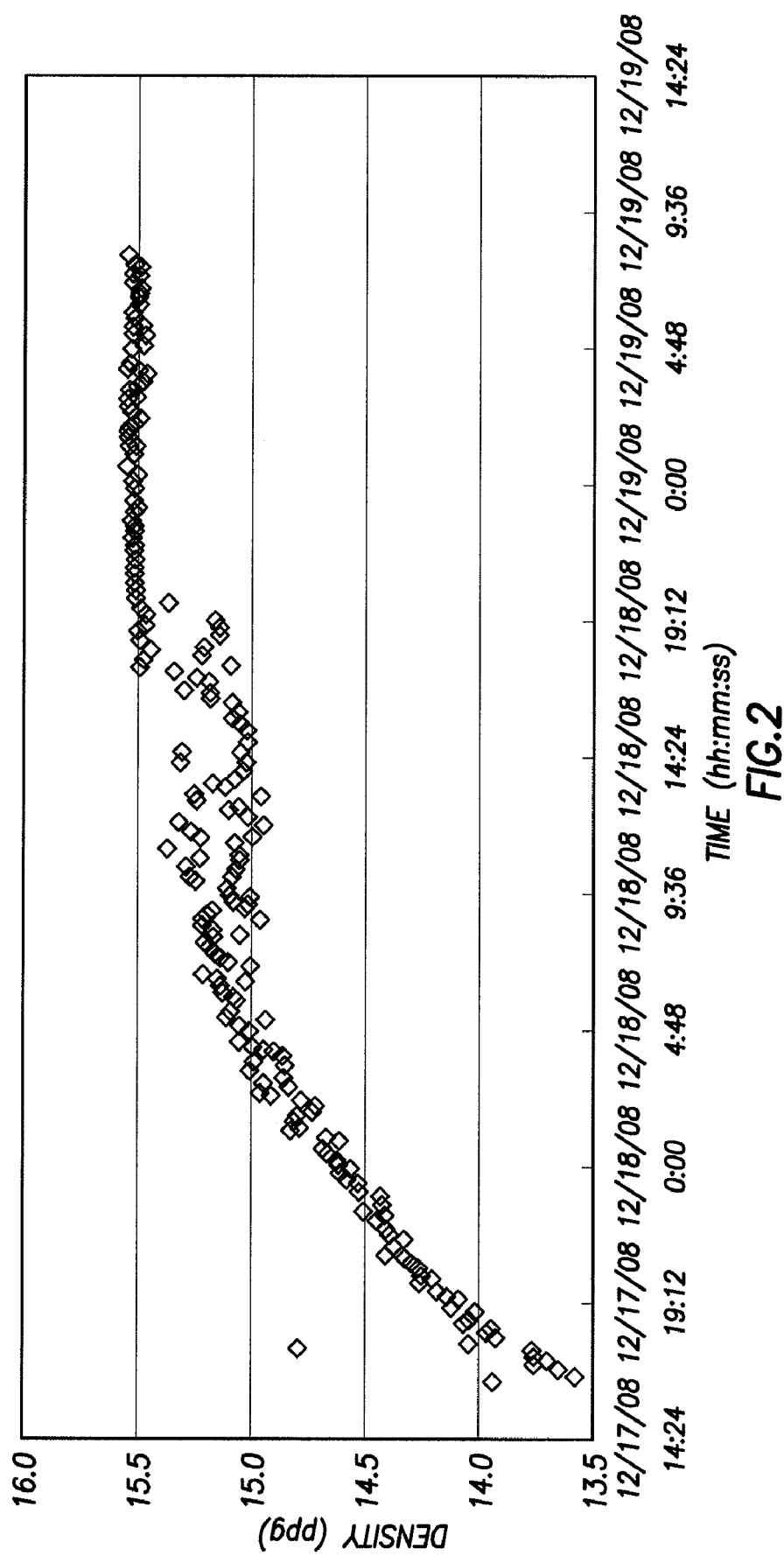
FIG. 2 is a chart of the change in measured density over time for a fluid sample obtained using a Sag Measurement System in accordance with an exemplary embodiment of the present invention.

An SMS in accordance with an exemplary embodiment of the present invention was used to analyze the sag performance of a drilling fluid with barite as the weighing material. As depicted in FIG. 2, the information obtained from the density transducer of the SMS was then used to plot the change in the density of the drilling fluid being circulated through the SMS as a function of time.

As depicted in FIG. 2, the density of the drilling fluid in the lower area of the test container increased from about 13.6 lb/gal to about 15.5 lb/gal in about 30 hours. Moreover, the chart indicates that the density signature with time converges to a limit of about 15.5 lb/gal.

Example II

The data set of Example I was used to determine the settling rate of the solids in the sample. Specifically, the data obtained from the density transducer of the SMS over the first two hours of the analysis conducted in Example I was used to determine the settling velocity of the barite. The following values were used in making that calculation: % Oil=80; $D_{brine}$=1.231 g/cm$^3$; R=3.81 cm; t=2 hours; $Vol_{mixed}$=476 cm$^3$. The following table indicates the results obtained over the 2 hour period:

| Time | Density (lb/gal) | φ (from Eq. 2) | Settling Velocity$_{barite}$ (mm/hr) |
|---|---|---|---|
| 16:36 | 13.598 | 0.257 | |
| 18:36 | 14.038 | 0.275 | 3.9 |

Example III

Using the system and methods disclosed herein, the size of the grains in a barite sample which would settle was determined. In this example, the upper portion of the test container which contained the unmixed portion of the fluid had a volume of about 2204 cm$^3$. The lower portion of the test container which contained the mixed portion of the fluid had a volume of about 476 cm$^3$. Using Eq. 2, the initial and final density in the mixed section and the volume fraction increase of barite was then calculated as:

Test Section Volume=2204 cm$^3$

Mixed Section Volume=476 cm$^3$

Initial Barite Volume fraction=0.218 (assuming $D_{barite}$=4.23 g/cm$^3$)

Final Barite Volume fraction=0.287

Differential Volume fraction=0.068

$D_{barite}$=4.23 g/cm$^3$

Using the above values, when the density stopped increasing, the increase in the mass of the barite in the test section, $M_{increase}$, was calculated as:

$M_{increase}$=0.068(476)4.23=136.9 g

Figure 3:
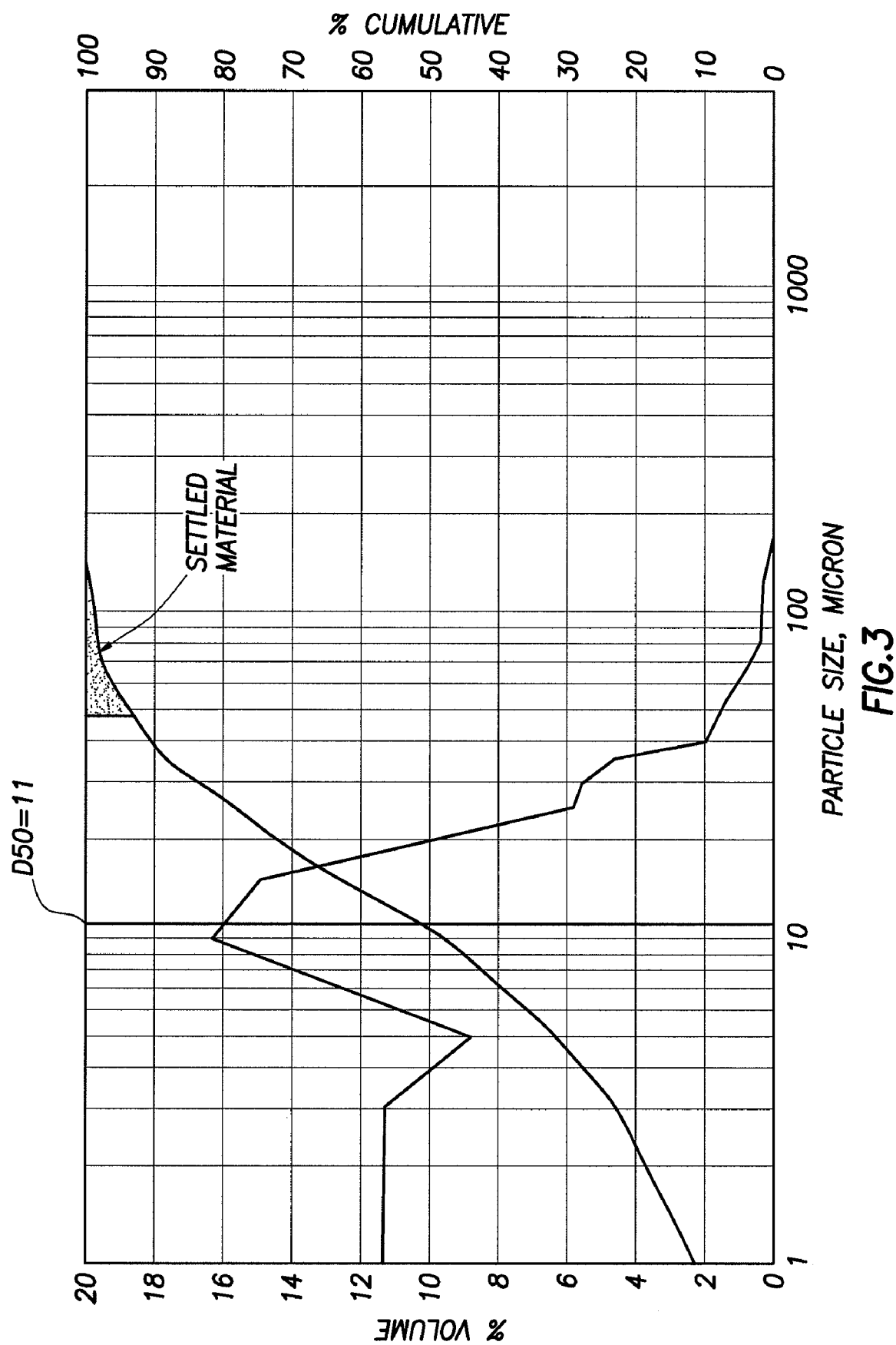
FIG. 3 is a chart depicting the relationship between particle size distribution and material settlement for a sample analyzed in accordance with an exemplary embodiment of the present invention.

This mass increase represents 32.4 cm$^3$ of barites. The initial barite volume fraction was 0.218 of 471.7 cm$^3$. As a result, 32.4 cm$^3$ of the 471.7 cm$^3$ that was originally in the test section would have needed to settle to increase the density. This indicates that about 6.9% of the barite volume in the upper section would have settled. Assuming that the larger particles settle faster than the smaller particles and that there is no particle agglomeration, then all the settled volume would be represented by particles in the larger size ranges of the PSD. Accordingly, as shown in the PSD curve of FIG. 3, particles with a size of about 50 microns and larger would have settled.

Therefore, the present invention is well-adapted to carry out the objects and attain the ends and advantages mentioned as well as those which are inherent therein. While the invention has been depicted and described by reference to exemplary embodiments of the invention, such a reference does not imply a limitation on the invention, and no such limitation is to be inferred. The invention is capable of considerable modification, alteration, and equivalents in form and function, as will occur to those ordinarily skilled in the pertinent arts and having the benefit of this disclosure. The depicted and described embodiments of the invention are exemplary only, and are not exhaustive of the scope of the invention. Consequently, the invention is intended to be limited only by the spirit and scope of the appended claims, giving full cognizance to equivalents in all respects. The terms in the claims have their plain, ordinary meaning unless otherwise explicitly and clearly defined by the patentee.

What is claimed is:

1. A method determining settling velocity in a fluid mixture comprising:
    determining a first density of the fluid mixture at a first point in time;
    inferring a first volume fraction of a solid component of the fluid mixture at the first point in time;
    determining a second density of the fluid mixture at a second point in time;
    inferring a second volume fraction of the solid component of the fluid mixture at the second point in time; and
    using a difference between the first volume fraction and the second volume fraction to determine the settling velocity of the solid component in the fluid mixture.

2. The method of claim 1, wherein determining the first density of the fluid mixture and the second density of the fluid mixture comprises:
    placing the fluid mixture in a test container having a lower portion and a higher portion;
    directing the fluid mixture to a density transducer in a circulation loop through a suction port at the lower portion of the test container; and
    returning the fluid mixture to the test container from the circulation loop through a return port at the lower portion of the test container.

3. The method of claim 1, wherein determining the first density of the fluid mixture and the second density of the fluid mixture comprises:
    placing the fluid mixture in a test container having a plurality of sets of ports;
        wherein each of the plurality of sets of ports comprises a suction port and an associated return port both located at substantially the same vertical position on the test container;
    directing the fluid mixture to a density transducer in a circulation loop through a selected suction port of one of the plurality of the sets of ports of the test container; and
    returning the fluid mixture to the test container from the circulation loop through the return port associated with the selected suction port.

4. The method of claim 1, wherein the fluid mixture is a drilling fluid.

5. The method of claim 1, wherein the solid component is a barite solid.

* * * * *

UNITED STATES PATENT AND TRADEMARK OFFICE
CERTIFICATE OF CORRECTION

PATENT NO. : 8,387,442 B2  
APPLICATION NO. : 12/685348  
DATED : March 5, 2013  
INVENTOR(S) : Dale E. Jamison and Robert J. Murphy It is certified that error appears in the above-identified patent and that said Letters Patent is hereby corrected as shown below:

In the Claims

Column 9, line 19, Claim 1:

Insert --of-- between "A method" and "determining" in the first line of Claim 1.

Signed and Sealed this
Fourth Day of November, 2014

Michelle K. Lee
*Deputy Director of the United States Patent and Trademark Office*